(12) United States Patent
Stiles

(10) Patent No.: US 6,558,359 B1
(45) Date of Patent: May 6, 2003

(54) HEART MUSCLE IRRIGATION DEVICE, APPLICATOR AND METHOD

(76) Inventor: Frank B. Stiles, Box 3016, 78 Regency Point Drive, Saywood Estates, Truro, N. S. (CA), B2N 6L1

(*) Notice: Subject to any disclaimer, the term of this patent is extended or adjusted under 35 U.S.C. 154(b) by 0 days.

(21) Appl. No.: 09/378,723

(22) Filed: Aug. 23, 1999

Related U.S. Application Data

(63) Continuation-in-part of application No. 08/965,382, filed on Nov. 6, 1997, now abandoned.
(60) Provisional application No. 60/031,254, filed on Nov. 12, 1996.

(51) Int. Cl.$^7$ ................................................ A61M 5/24
(52) U.S. Cl. .................................... 604/203; 604/164.06
(58) Field of Search ............................... 604/274, 275, 604/278, 279, 164.06, 164.09, 95.01, 95.02, 44, 188, 201–203, 891.1, 276, 536, 35

(56) References Cited

U.S. PATENT DOCUMENTS 5,098,411 A * 3/1992 Watson et al. .............. 604/268
5,224,952 A * 7/1993 Deniega et al. ..... 604/164.06 X

* cited by examiner

*Primary Examiner*—Anhtuan T. Nguyen
(74) *Attorney, Agent, or Firm*—Robert A. Wilkes

(57) ABSTRACT

A heart muscle irrigation device comprises a short rivet like member with one closed and one open end, and a barrel including a plurality of holes, slots, an area mesh, or a grid. The irrigation device is inserted into the heart muscle so as to provide a channel from, for example, the left ventricle, to provide ad adequate oxygenated blood supply to a starved muscle. The irrigation device is inserted from either outside or inside the rib cage by an insertion device. The insertion device comprises a plunger and barrel assembly adapted to contain the irrigation device. The tip of the insertion device includes members adapted to penetrate the heart muscle. If the irrigation device is inserted through an insertion into the rib cage, an applicator comprising a tubular member with a planar tip including a soft elastomeric seal can be used whereby a portion of the heart muscle is held more or less rigidly for the short period during which the irrigation device is inserted. These devices, even when a rib cage insertion is made, do not require either the life support systems or the extensive rib cage damage associated with conventional bypass surgery.

11 Claims, 4 Drawing Sheets

HEART MUSCLE IRRIGATION DEVICE, APPLICATOR AND METHOD

This application is a continuation-in-part of U.S. application Ser. No. 08/965,382 filed Nov. 6, 1997, now abandoned which claims benefit of Ser. No. 60/031,254 filed Nov. 12, 1996.

BACKGROUND OF THE INVENTION

This invention relates to a device, and to a method of using the device, to improve blood flow to the heart muscles. When heart muscles are relatively speaking starved of blood, they are also starved of oxygen, which is carried to them by the blood flow. If a condition in which an inadequate blood flow occurs is allowed to continue to exist for any extended period of time, the heart muscles are in danger of rapid and severe damage, to a point which can be, or can become, life threatening. At present, the most often used therapy to alleviate such a condition is by-pass surgery. This procedure involves significant risk to the patient and is therefore not lightly undertaken.

This invention seeks to provide an alternative procedure whereby a blood flow can be established to the heart muscles directly. This procedure can be applied to the heart as part of cardiac surgery, when the chest cavity has been opened to provide direct access to the heart muscles. Alternatively, this procedure can be applied through the chest wall, with only a relatively small incision.

In outline, the irrigation device of this invention is somewhat similar to a small, open ended hollow rivet which has openings or perforations in its cylindrical side wall. By using an insertion device that is similar to a hypodermic syringe, the rivet is inserted into the heart muscle so that the closed end is more or less flush with the outside of the muscle, and the open end is located to receive aerated blood. The blood then flows to the heart muscle through the openings in the cylindrical wall.

Thus in a first embodiment this invention provides a heart muscle irrigation device comprising a hollow substantially cylindrical body having a first closed end and a second open end, the first and second ends each also including radially extending head members, and the cylindrical body having a plurality of radially oriented apertures there through, wherein the head members attached to both the first and the second ends are sufficiently flexible to be bent from a radially extending position, to a position substantially in line with the outside surface of the cylindrical hollow body.

In a second broad embodiment this invention comprises an insertion device for the heart irrigation device comprising a barrel having a first open end and a second end; flexible means attached to the second end which in a first closed position is adapted to penetrate a heart muscle to provide an opening, and which in a second open position allows passage of an irrigation device contained in the barrel; and plunger means inserted through the first open end of the barrel adapted to eject an irrigation device from the barrel and into engagement with an aperture in the heart muscle.

In a third broad embodiment this invention provides a method for improving blood flow to heart muscles comprising; providing an insertion device in the barrel of which a muscle irrigation device has been inserted with its open end toward the second end thereof, the internal diameter of the barrel being sized to accept the irrigation device with its head members bent from a radially extending position; inserting the second end of the insertion device into and through a selected heart muscle; and simultaneously ejecting the irrigation device through the second end of the insertion device, and withdrawing the insertion device, thus locating the irrigation device in the aperture created in the heart muscle by the insertion device.

DESCRIPTION OF THE PREFERRED EMBODIMENTS

The invention will now be described with reference to the attached drawings in which.

Figure 1:
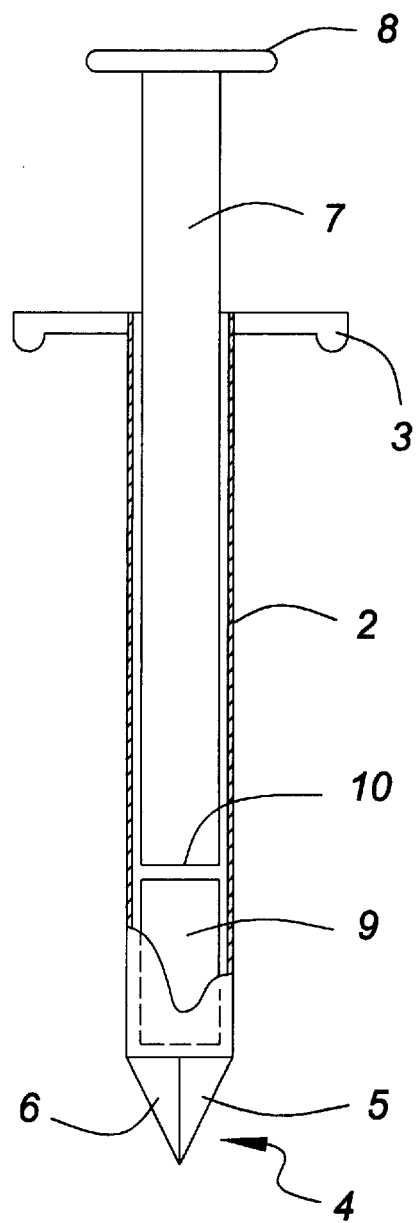
FIG. 1 shows partly sectioned a simple insertion device.

Referring first to FIG. 1, the insertion device 1 is in essentially two parts. The outer barrel 2 is substantially cylindrical, and has attached at, or near, its first open end a pair of finger grips 3. At it second end there is a sharp head 4 which includes a plurality of somewhat petal shaped flexible members 5 and 6. Two such members are shown; in practice four or even six are used. Inside the barrel is a plunger 7, with a head 8. Adjacent the second end of the barrel is the irrigation device, which is also close to the end 10 of the plunger 7.

When used, the head 4 is eased into the heart muscle to form an aperture therein. Its placement into the muscle is carefully monitored by known imaging means. It is inserted until the head 4 has entered a heart chamber or ventricle which contains oxygenated blood. The plunger is then used to eject the irrigation device by deflecting the head parts 5, 6, etc., whilst at the same time slowly withdrawing the insertion device. By coordinating the movement inwardly of the plunger 7, and outwardly of the barrel 2, the irrigation device is left inserted into the aperture made in the heart muscle by the head 4.

Figure 2:
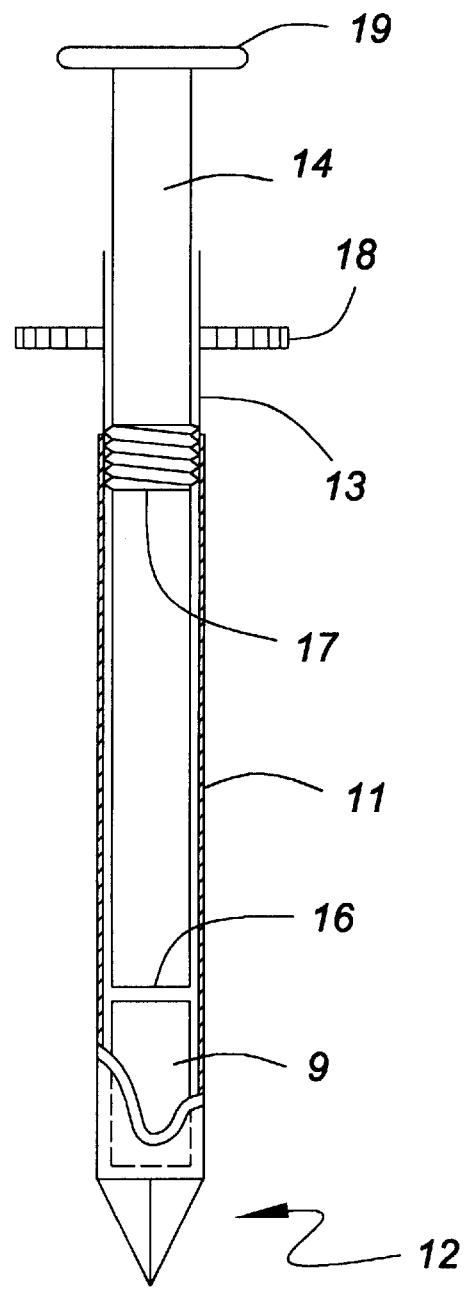
FIG. 2 shows partly sectioned a more complex insertion device.

In FIG. 2 a more sophisticated insertion device is shown. This comprises an outer barrel 11, to which is attached a head unit 12. An inner barrel 13 is a sliding fit into the outer barrel 11. A plunger 14 is fitted inside the inner barrel, as also is the irrigation device 9 adjacent the end 16 of the plunger 14. The plunger is located in the inner barrel by the mating male and female threads shown at 17.

This insertion device is used in more or less the same fashion as that of FIG. 1, but there is more control over the ejection of the irrigation device 9. After the insertion has been placed through the heart muscle, thus providing the required aperture, the irrigation device is ejected by rotating the turnwheel 18 whilst holding the head 19. As a consequence of the rotation, the plunger 14 is urged by the mating threads 17 toward the irrigation device 9, thus ejecting the irrigation device through the head 12.

Figure 3:
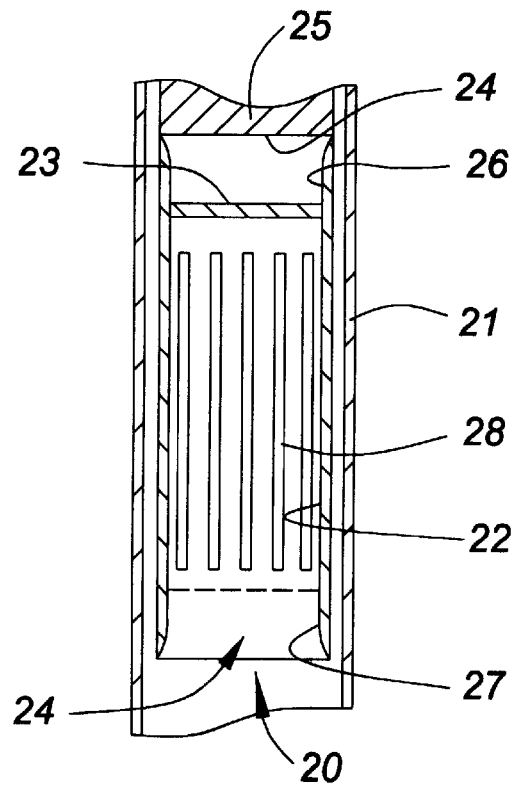
FIG. 3 shows an irrigation device mounted into the barrel of an insertion device.

In FIG. 3 there is shown an irrigation device mounted, ready for use, in a barrel 21. This barrel 21 can be either of those shown in FIG. 1 or 2. The irrigation device 20 includes a cylindrical body portion 22, a first closed end 23, and a second open end 24. The body portion 22 is a sliding fit into the barrel 21. The closed end 23 of the body portion is located adjacent the end 24 of a plunger 25. It can also be seen that when loaded into the insertion device the two radial members 26 and 27 are each bent inwardly from the radial position (see FIG. 4) to be essentially coaxial with the body portion 22, but pointing in opposite directions. This serves to locate the irrigation device in the insertion device whilst it is being assembled, amongst other things. This irrigation device is also provided with a plurality of slots 28 to enable blood to reach the heart muscle tissues from the hollow interior of the body portion 22.

Figure 4:
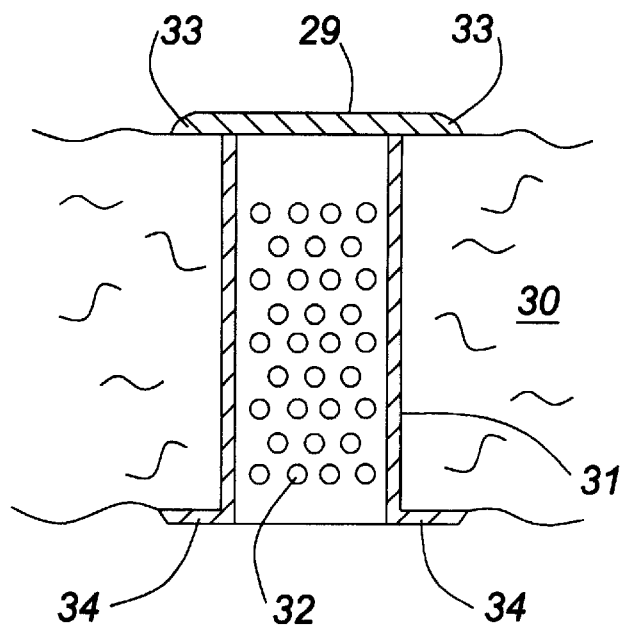
FIG. 4 shows schematically a second irrigation device after placement into a heart muscle.

In FIG. 4 there is shown schematically a different irrigation device 29 lodged into a heart muscle 30. The body portion wall 31 is provided with a plurality of small holes 32 allowing blood access to the tissues of the muscle 30 via the said holes, slots, an area mesh or a grid and hence on into and through the continuously expanding number of collateral blood delivery vessels. As shown a unitary construction is used; a plurality of suitable small holes is also obtainable in a three part construction, in which a portion of the body wall comprises a suitable mesh material. The irrigation device is held in place by the members 26, and 27, which have returned to their essentially radial positions; this happens at each end as the irrigation device is ejected from the barrel.

Whilst the injection device can be used on its own, and indeed would be so used in emergency situations, it is advantageous to be able to hold the heart muscle more or less rigid whilst the irrigation device is being placed. A suitable applicator is shown in FIGS. 5–9.

Figure 5:
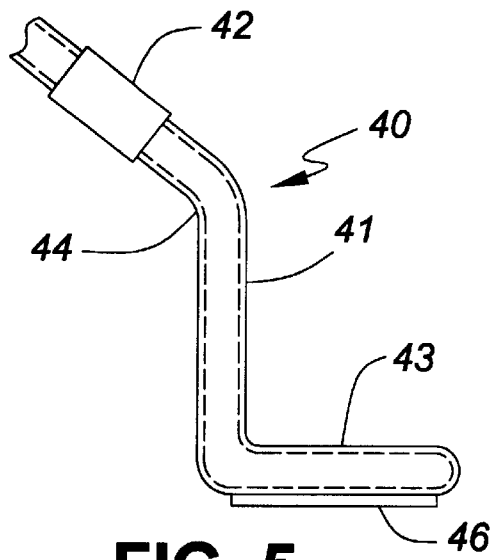
FIG. 5 shows a side view of an applicator for use with the insertion devices of FIGS. 1 and 2.

Referring first to FIG. 5, applicator 40 has a hollow shaft 41 which conveniently has a soft elastomer handle 42. One end of the hollow shaft is provided with a suitable attachment for a surgical vacuum device (not shown). At the other end the hollow tube a substantially planar tip face 43 extends from the handle. For ease of use, the tip should be at an angle of about 45° to the axis of the hollow shaft. This angle is not critical, and other angles both higher and lower could be used: the angle facilitates location the insertion device more or less perpendicular to the heart muscle. The angle can be obtained in any suitable way: the hollow shaft can include a bend as at 44, or, as shown at 45 in FIG. 7, the hollow shaft can be attached to the tip at a suitable angle. The tip is also of tubular construction, and communicates with the hollow shaft. The underside of the tip has a layer of soft elastomeric material 46 attached to it. The construction of the shaft and of the tip is discussed further below in the context of FIG. 10.

Figure 6:
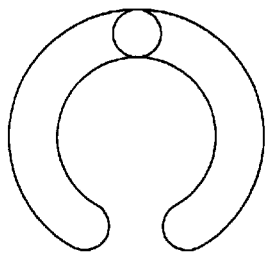
FIGS. 6 and 7 show top views of two end structures for the applicator of FIG. 5.
Figure 7:
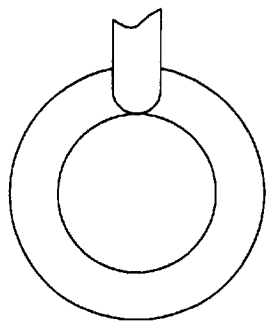

The tip itself as shown in FIGS. 6 and 7 is of more or less circular shape: in FIG. 6 the tip 47 is an arc of a circle which is somewhat like a horseshoe; other suitable shapes are possible. Further, in FIG. 6 the tubular member is shown attached more or less at the centre of the horseshoe as this appears to be the most convenient location; other locations are also possible.

Figure 8:
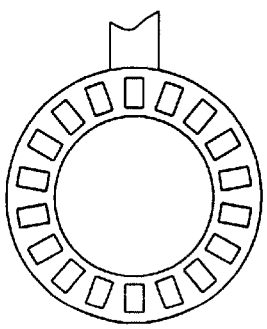
FIGS. 8 and 9 show the construction of the underside of the end structures.
Figure 9:
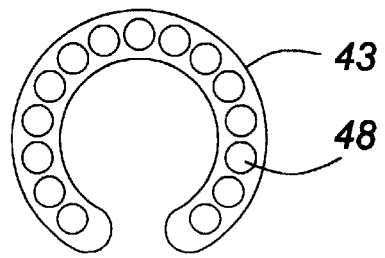

The underside of the tip is foraminous: in FIG. 9 is shown a pattern of holes 48, and in FIG. 8 is shown a series of slots 50. Other arrangements such as in inserted mesh or grid are also possible. In FIGS. 8 and 9 the soft elastomer layer 46 is omitted for clarity. It is either provided with a set of holes to match those in the underside of the tip, or it can, for example, be provided with a slot.

Figure 10:
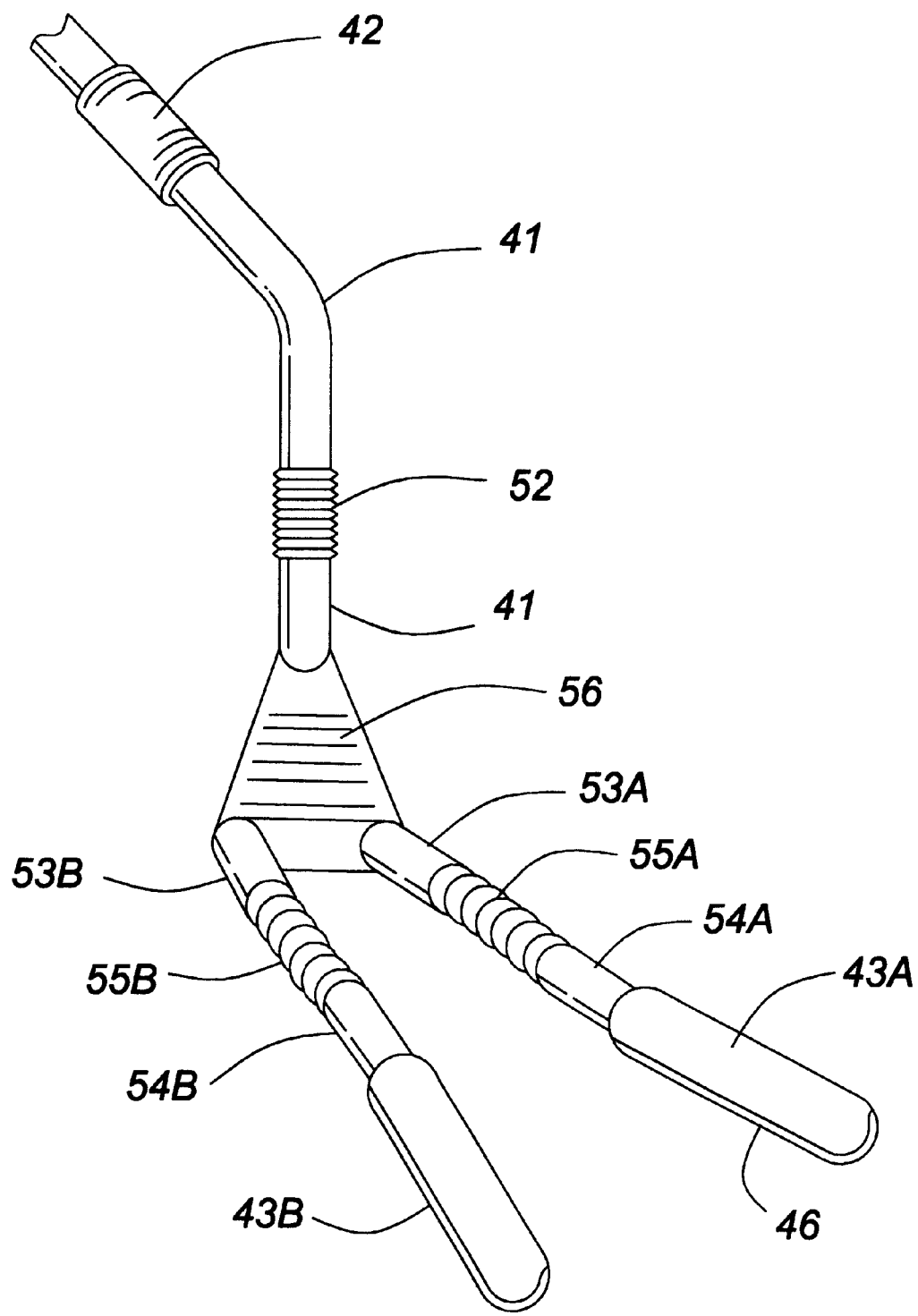
FIG. 10 shows an alternative construction for the applicator.

An alternative construction is shown in FIG. 10. This construction is still based on a vacuum tube 41, which carries a soft elastomer handle 42. Instead of a single tip 43 provided with a soft elastomer layer 46, two separate tips 43A and 43B are provided, each having a soft elastomer layer 46 (the layer for tip 43B is not visible). Each tip is connected to the hollow shaft 41 by a short hollow shaft including a first tubular part 53A, 53B, a flexible part 55A, 55B and a second short tubular part 54A, 54B. The first two tubular parts are both connected into an adapter 56, which is attached to the hollow shaft 41. Additionally, the hollow shaft 41 includes a flexible portion 52. Further, if desired the three joints between the hollow shaft 41 and the two short tubular parts 53A and 53B are constructed so that any or all of them can rotate relative to the adapter 56. Rotatable joints of this type are well known. In FIG. 10 the three flexible parts 52 , 53A and 53B are shown as ribbed concertina-like elements: it is also contemplated that each of them can be made by using a plastics material which will provide a tube which is both stiff enough not to collapse under the applied vacuum, and which is flexible enough to be bent into and then retain a desired configuration. Surgically acceptable plastics materials of this type are well known. The same type of plastics material can also be used for the two tips 43A and 43B, and for the other constructions described above if desired.

The advantage of this more complex construction is twofold. First, the ability to bend the applicator as a whole allows the surgeon both to place it more accurately and with a better seal to the heart muscle, and to locate the vacuum supply so as not to interfere with the operation. Second, by separating the single tip into two parts the applicator can be used to hold a heart muscle on either side of a heart surface blood vessel, as it will bridge over the blood vessel.

To use the applicator and insertion device together, an insertion is first made in the patient's left rib cage, preferably between the appropriate ribs, for example to provide access to the left heart ventricle muscle. This incision is of an appropriate length, and will generally be not more than 75 mm. in length. An applicator with a vacuum supply attached is then applied to the surface of the heart muscle, so that sufficient vacuum is applied to hold a small portion of the live and beating heart muscle reasonably still and rigid for the short time required to insert the irrigation device. The soft elastomer layer on the underside of the applicator serves as a seal between the applicator tip and the muscle surface.

This procedure has the advantages that although an incision into the chest cavity is required, it is far smaller than that used for bypass surgery, and does not involve any severance of either the sternum or the rib cage. Further, life support systems are not needed whilst the irrigation device is being inserted, as the patient's heart is not closed down or stopped. As the incision is relatively short, the risk to the patient is minimized, the time required for the surgical procedure is minimized, and the patient's recovery time compared to bypass surgery significantly shortened.

Both the injection device and the applicator are each suitably made from any surgically acceptable material having adequate strength, and which can be adequately sterilized. Such materials are well known in the art. The irrigation device can be made as one unitary part, or from several parts. The two radial members must be adequately flexible, and a fibre reinforced elastomer material is therefore preferred. The hollow body portion can be fabricated from the same material, or it can be made from a more solid material. However, it should also be borne in mind that the irrigation device should be able to flex to some extent so as to accommodate movement of the heart muscle without causing damage to it. It would therefore appear that although fabrication of at least the hollow body portion from a metal such as a surgically acceptable stainless steel is possible, this might not be desirable as such a material may cause muscle damage. The irrigation device must be made from a material which will not be rejected by the body: suitable materials are well known in the art.

The head such as 4 in FIG. 1 presents a different problem. The material used must be capable of being made sharp enough at least at the tip to penetrate the heart muscle. It must also be flexible enough the allow the irrigation device to be ejected. A thin stainless steel assembly is preferred.

In the hollow body, the choice of aperture is quite wide: both perforations and slots are shown, but other methods can be used. The main requirement is to provide adequate blood flow without impairing the structural integrity of the hollow body. It is also contemplated that the irrigation device will be made in several lengths and diameters, to suit different heart muscles.

I claim:

1. A heart muscle irrigation device comprising a hollow substantially cylindrical body having a first closed end and a second open end, the first and second ends each also including radially extending head members, and the cylindrical body having a plurality of radially oriented apertures there through, wherein the head members attached to both the first and the second ends are sufficiently flexible to be bent from a radially extending position, to a position substantially in line with the outside surface of the cylindrical hollow body.

2. An irrigation device according to claim 1 wherein the radially oriented apertures comprise a plurality of holes.

3. An irrigation device according to claim 1 wherein the radially oriented apertures comprise a plurality of slots.

4. An irrigation device according to claim 1 wherein the radially oriented apertures comprise a mesh incorporated into the cylindrical body.

5. An insertion device, for a heart muscle irrigation device, which insertion device comprises a barrel having a first open end and a second end; a sharp head attached to the second end of the barrel which in a first closed position is constructed and arranged to penetrate a heart muscle to provide an opening, and which in a second open position is constructed and arranged to allow passage of a heart muscle irrigation device contained in the barrel; and a plunger inserted through the first open end of the barrel, movement of which ejects the irrigation device from the barrel and into engagement with the opening in the heart muscle.

6. An insertion device according to claim 5 including a cap attached to the plunger and cooperating finger grips attached adjacent the open first end of the barrel.

7. An insertion device according to claim 5 wherein the flexible means comprises a plurality of petal shaped members.

8. An insertion device according to claim 7 including two, four, or six petal shaped members.

9. An insertion device according to claim 5 wherein the plunger adapted to eject an irrigation device from the barrel includes cooperating screw thread means between the plunger and the barrel, and a turn wheel attached to the plunger, in which ejection of the heart muscle irrigation deice from the second end of the barrel is effected by rotation of the turn wheel.

10. A method for providing blood flow to heart muscles comprising: providing an insertion device in the barrel of which a muscle irrigation device has been inserted with its open end toward the second end thereof, the internal diameter of the barrel being sized to accept the irrigation device with its head members bent from a radially extending position; inserting the second end of the insertion device into and through a selected heart muscle; and simultaneously ejecting the irrigation device through the second end of the insertion device, and withdrawing the insertion device, thus locating the irrigation device in the aperture created in the heart muscle by the insertion device.

11. A method according to claim 10 including the further steps of creating an incision providing access to the selected heart muscle; applying an applicator to the heart muscle; applying vacuum to the heart muscle by means of the applicator; and inserting the irrigation device into the selected area of heart muscle to which vacuum has been applied.

* * * * *